United States Patent
Koch et al.

(10) Patent No.: US 6,544,191 B2
(45) Date of Patent: Apr. 8, 2003

(54) PROCESS FOR DETERMINING THE FUNCTIONAL RESIDUAL CAPACITY OF THE LUNGS

(75) Inventors: Jochim Koch, Ratzeburg (DE); Dieter Weismann, Gross-Grönau (DE); Georg Ankerhold, Aalen-Unterkochen (DE); Horst-Dieter Hattendorff, Bad Schwartau (DE)

(73) Assignee: Dräger Medizintechnik GmbH (DE)

( * ) Notice: Subject to any disclaimer, the term of this patent is extended or adjusted under 35 U.S.C. 154(b) by 2 days.

(21) Appl. No.: 09/902,905

(22) Filed: Jul. 11, 2001

(65) Prior Publication Data

US 2002/0052560 A1 May 2, 2002

(30) Foreign Application Priority Data

Sep. 20, 2000 (DE) .......................... 100 46 465

(51) Int. Cl.⁷ .................................. A61B 5/08
(52) U.S. Cl. ...................... 600/538; 600/529
(58) Field of Search .................. 600/529, 532, 600/538; 73/23.3; 422/84

(56) References Cited

U.S. PATENT DOCUMENTS

| | | | |
|---|---|---|---|
| 4,307,730 A | * | 12/1981 | Korn ........................ 600/541 |
| 5,540,233 A | * | 7/1996 | Larsson et al. ............ 600/538 |
| 6,139,506 A | * | 10/2000 | Heinonen .................. 600/532 |

FOREIGN PATENT DOCUMENTS

EP 0 653 183 B1 5/1995

* cited by examiner

Primary Examiner—Robert L. Nasser
Assistant Examiner—Patricia C Mallari
(74) Attorney, Agent, or Firm—McGlew and Tuttle, P.C.

(57) ABSTRACT

A process is provided for determining the functional residual capacity (FRC) of the lungs during respiration. An environmentally friendly trace gas is used in a process and system for determining the FRC by using fluoropropanes as a trace gas. Values for the FRC can thus be calculated, resolved for individual breaths, from the expiratory trace gas concentration and the expired breathing gas volume and they can be used for determining the FRC depending on their convergence behavior.

10 Claims, 3 Drawing Sheets

PROCESS FOR DETERMINING THE FUNCTIONAL RESIDUAL CAPACITY OF THE LUNGS

FIELD OF THE INVENTION

The present invention pertains to a process for determining the functional residual capacity (FRC) of the lungs during respiration. The determination of the FRC during respiration therapy in general and during the diagnosis of the maturity of the lungs of respirated premature and newborn babies in particular may be helpful in the initiation and the monitoring of the necessary therapeutic measures. At the same time, disturbances in the intrapulmonary gas distribution can be quantified by such a process.

BACKGROUND OF THE INVENTION

The functional residual capacity (FRC) is considered to be an important, informative variable for the respiration of a patient; however, its measurement has not yet found acceptance in routine clinical practice because of the rather complicated apparatus required. The measurement of the FRC has only been known from the area of clinical experiments so far.

The determination of the FRC can be carried out in a patient in various ways. A method known for healthy patients in the lung function laboratory is body plethysmography, in which the patient is sitting in an airtightly closed chamber and the lung volume can be determined on the basis of the breath-dependent variations in the air pressure in the chamber. This method is very complicated and cannot be used in intensive care patients.

Another method is the so-called wash-out method. In an open breathing circuit, either the nitrogen contained in the lungs or an inert gas washed in before, usually a gas that is poorly soluble in blood, is washed out by another gas, i.e., replaced by that gas. Nitrogen wash-out methods, noble gas wash-out methods, and sulfur hexafluoride wash-out methods operate according to this principle. The FRC is calculated by measuring the amount of indicator gas washed out and its concentration in the lungs before and after the wash-out, the FRC being obtained as the quotient of the indicator gas volume washed out and the difference between the indicator gas concentration before the wash-out and the indicator gas concentration after the wash-out. The indicator gases used shall not induce any physiological, toxic or metabolic reactions in the patient's lungs. Moreover, they shall not be possibly soluble in the blood in order not to distort the mass balance, on which the calculation of the FRC according to the wash-out method is based.

To determine the FRC by means of nitrogen wash-out, an increased oxygen concentration, e.g., 100 vol. %, is supplied for the patient for a short time or part of the nitrogen is replaced with a noble gas at constant oxygen concentration. Contrary to the nitrogen wash-out by means of noble gases, no additional gas is needed in a respirator for the nitrogen wash-out by means of an increased oxygen concentration because oxygen and normal breathing air are normally available there. However, there are reservations against increasing the oxygen concentration in the case of use for premature and newborn babies because of the suspicion that retrolental fibroplasia may develop in this case, which may subsequently lead to loss of eyesight. Conversely, the oxygen concentration cannot be reduced without problems in the case of intensive care patients, who need a high oxygen concentration, without running the risk of inadequate oxygen supply. Moreover, the measurement of the nitrogen concentration during the wash-out is technically very complicated, because nitrogen is difficult to detect. It can be carried out, e.g., with a mass spectrometer. Laughing gas, $N_2O$, has been used as an inhalation anesthetic for a long time. Due to its light absorption behavior, it can be detected relatively rapidly and accurately by infrared optical measurement methods. It is therefore logical to use laughing gas at low concentrations as a trace gas for determining the FRC. However, laughing gas is rapidly absorbed by the blood and a considerable percentage of laughing gas, about 40%, cannot therefore be washed out directly, as a result of which the mass balance necessary for the determination of the FRC is distorted.

The wash-out method can also be carried out with so-called trace gases, e.g., noble gases, instead of nitrogen. Noble gases, e.g., helium or argon, are well suited for the determination of the FRC for physiological reasons. They are inert, they have neither toxic effect nor, at low concentrations, anesthetic effect and only insignificant quantities of these gases are dissolved in the blood. They are not combustible and are thermally stable. With such a wash-out method, the noble gas is first administered at a low concentration, e.g., 1 vol. %, during the respiration of the patient, until an equilibrium becomes established in the lung. The metering is then switched off and the noble gas is subsequently washed out with normal breathing air. The concentration and the volume flow of the expired air are now measured continuously. If noble gases are used as a trace gas, mainly mass spectrometers, which are unsuitable for routine clinical use, are likewise used for the concentration measurement.

Methane and butane may also be used as trace gases to determine the FRC. They are physiologically harmless at low concentrations and they can be readily detected according to infrared optical methods. The drawback is that methane and butane are combustible and are explosive at certain mixing ratios. An explosive mixing ratio is formed, e.g., by 4.1 vol. % of methane in usual breathing air. Contrary to the determination of the FRC in spontaneously breathing patients, a higher oxygen concentration is often necessary in intensive care patients than the concentration of about 21 vol. % normally present in the air. However, the risk of explosion also increases markedly with increasing oxygen concentration in the case of methane and butane, so that the concentration of these gases must be very low to avoid an explosive gas mixture. In light of such risks, the use of methane and butane is not indicated, especially in intensive care medicine.

As an alternative to wash-out, it is also possible to analyze the wash-in of trace gas, i.e., to set up the net balance of the trace gas flowing into the patient's lung, by means of concentration and volume flow measurements.

To determine the FRC according to a wash-out method as well as a corresponding wash-in method, inert trace gases that are harmless for the patient are therefore sought, which can be measured with a small sensor near the patient. The sensor itself must have a very rapid time response. The response must take place in less than 25 msec in the case of the respiration of newborn babies, because a sufficient resolution of the curve showing the trace gas concentrations over time, which is necessary for the determination of the FRC according to the wash-out method, is only possible under these conditions. If the sensor is arranged in the main stream of the breathing circuit, it should be as small as possible in order not to needlessly increase the dead space, which would lead to an impairment of the quality of respiration. An increased dead space leads to the less satisfactory wash-out of carbon dioxide and therefore to hypercapnia, especially in premature and newborn babies.

Sulfur hexafluoride is mentioned as a trace gas in EP 0 653 183 B1. Sulfur hexafluoride, $SF_6$, has been known for a long time as a trace gas for the determination of the FRC. Sulfur hexafluoride is considered to be inert and can be easily detected by means of infrared optical gas sensors; it absorbs in the wavelength range of 10.6 µm.

One drawback of sulfur hexafluoride is that it can lead to very high absorption of sunlight at high altitudes of the atmosphere and thus to warming of the environment. Sulfur hexafluoride is therefore discussed in connection with the "greenhouse effect." Whenever possible, it should be replaced with more environmentally friendly gases. Moreover, a TLV (Threshold Limit Value) of 0.1 vol. % is specified for sulfur hexafluoride.

SUMMARY AND OBJECTS OF THE INVENTION

The object of the present invention is to provide a trace gas for use for determining the functional residual capacity (FRC) of the lungs of a patient or test subject, which can be detected in a simple manner, is physiologically harmless and is environmentally friendly.

According to the invention, fluoropropane is used as a trace gas for determining the functional residual capacity (FRC) of the lungs during respiration. The fluoropropane may be a heptafluoropropane, a hexafluoropropane or a perfluoropropane.

According to another aspect of the invention, a process is provided for determining the FRC, in which a breathing gas containing a predetermined concentration of fluoropropane is introduced into the lungs during a wash-in phase until the lungs become saturated with the said fluoropropane and the corresponding volumes $V_1, \ldots, V_A$ of the expired breathing gas are determined for consecutive breaths $A=1, \ldots, n$ during the subsequent wash-out phase, the fluoropropane concentration in the expired breathing gas is measured with a said gas sensor, and a mean expiratory fluoropropane concentration $K_1, \ldots, K_A$ is determined from this by a computer for each breath $A=1, \ldots, n$. The process further comprises:

a) calculating the volume of fluoropropane having been expired until present since the beginning of the wash-out phase by the computer for each breath $A=1, \ldots, n$ as a sum of the individual volumes $V_1, \ldots, V_A$ of the expired breathing gas, and these volumes are multiplied by the corresponding mean fluoropropane concentration $K_1, \ldots, K_A$ of the fluoropropane in these volumes;

b) forming an $FRC_A$ value for the functional residual capacity (FRC) by the computer as a quotient of the expired volume of fluoropropane, which was calculated in step a), and the difference between the end tidal fluoropropane concentration $K_0$ at the beginning of the wash-out phase and the fluoropropane concentration $K_A$ at breath A.

Steps a) and b) may be repeated until a preset number of $FRC_A$ values calculated last are within a preset tolerance range. The present tolerance range may be 5% to 20% of the $FRC_n$ value calculated last.

The use of fluoropropanes as trace gases offers a number of advantages. Fluoropropanes have been known as propellants for spray cans, where they are considered to be substitutes for the fluorochlorohydrocarbons. Moreover, fluoropropanes are readily detectable by means of infrared optical measuring instruments because they markedly absorb infrared radiation in the wavelength range between 3 and 10 µm. Fluoropropanes are suitable for use as trace gases also because neither metabolic nor toxic effects on the human body are known. Their solubility in the blood is very low, and they are neither combustible nor explosive. They do not have anesthetic effect and the data currently available show that they do not pollute the environment and are not harmful for human health, either.

In a wash-out method for determining the functional residual capacity (FRC) with fluoropropane, a value is obtained for the FRC according to the formula $$FRC_A = \frac{1}{K_0 - K_A}(V_1 \cdot K_1 + \ldots + V_A \cdot K_A),$$

in which $A=1, \ldots, n$ are consecutive breaths since the beginning of the wash-out phase, $V_1, \ldots, V_A$ are the corresponding volumes of the expired breathing gas, and $K_1, \ldots, K_A$ are the fluoropropane concentrations determined for the given breath in the expired breathing gas. $K_0$ denotes the end tidal fluoropropane concentration at the beginning of the wash-out phase, which equals, e.g., 0.8%, and $K_n$ denotes that present at the last breath n taken into account.

In another advantageous variant of the method according to the present invention for determining the FRC, a physiologically substantiated break-off criterion is used for the measurements of the fluoropropane concentrations and the volumes in the expired breathing gas for determining the FRC, which is based directly on the convergence behavior of the values calculated for the FRC from the measured values.

If there are no disturbances in the gas distribution in the patient's lungs, the value $$FRC_1 = \frac{1}{K_0 - K_1} \cdot V_1 \cdot K_1$$

calculated for the functional residual capacity from the first breath during a wash-out phase also corresponds essentially to the further values calculated for the FRC from a plurality of consecutive breaths during the wash-out phase.

If there are disturbances in the gas distribution in the patient's lungs, the values $$FRC_1 = \frac{1}{K_0 - K_1} \cdot V_1 \cdot K_1$$

$$FRC_2 = \frac{1}{K_0 - K_2} \cdot (V_1 \cdot K_1 + V_2 \cdot K_2),$$

$$FRC_3 = \frac{1}{K_0 - K_3} \cdot (V_1 \cdot K_1 + V_2 \cdot K_2 + V_3 \cdot K_3),$$

$$\vdots$$

$$FRC_n = \frac{1}{K_0 - Kn} \cdot (V_1 \cdot K_1 + \ldots + Vn \cdot Kn)$$

for the functional residual capacity usually increase at the beginning and subsequently converge toward an end value. If such a convergence appears to develop, this is a meaningful break-off criterion for a method for determining the functional residual capacity (FRC) of the lungs.

The convergence of the $FRC_1, \ldots, FRC_n$ values can be recognized, e.g., from the fact that a preset number of $FRC_A$ values calculated last, e.g., of the three $FRC_{n-2}, FRC_{n-1}$ and $FRC_n$ values calculated last, is within a preset tolerance range. The tolerance range may be, e.g., 5% to 20% of the $FRC_n$ value calculated last. The $FRC_n$ value calculated last is the functional residual capacity.

On the one hand, the first breaths during the wash-out phase yield the highest concentrations and thus accurate values for the FRC because of the exponential decline of the fluoropropane concentration, and, on the other hand, precisely the first values are particularly sensitive with respect to disturbances in the gas distribution in the lungs. The evaluation of a plurality of breaths is therefore desirable in the case of disturbances in distribution. The values for the fluoropropane concentrations become very low during the breaths at the end of the wash-out phase and may already be in the range of the measuring uncertainty. Therefore, a breakdown is usually performed in practice according to certain criteria in the summation over the total amount of wash-out, e.g., when the values drop below the measuring uncertainty or after a set number of breaths.

The determination of the FRC can be initiated by the user individually or it can be preset automatically in a fixed time sequence in order to recognize, e.g., a longer trend under the effects of a respiration therapy.

Trace gas can be supplied for metering, e.g., from a, pressurized gas cylinder, in which a sufficient amount of trace gas is kept in reserve for a plurality of cycles, i.e., wash-ins. The gas heptafluoropropane has, e.g., a pressure of 2.9 bar at a temperature of 20° C. in a pressurized gas cylinder. It is now in this liquid phase and is available for metering in the liquid or gaseous form. The pressurized gas cylinder can be plugged into an adapter provided for this purpose, as a result of which a valve is opened at the same time at the tap or a diaphragm at the tap is also pierced. The pressurized gas cylinder can be removed from the adapter in the emptied state and refilled or reused.

The present invention will be explained in greater detail below on the basis of the exemplary embodiments shown in the drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
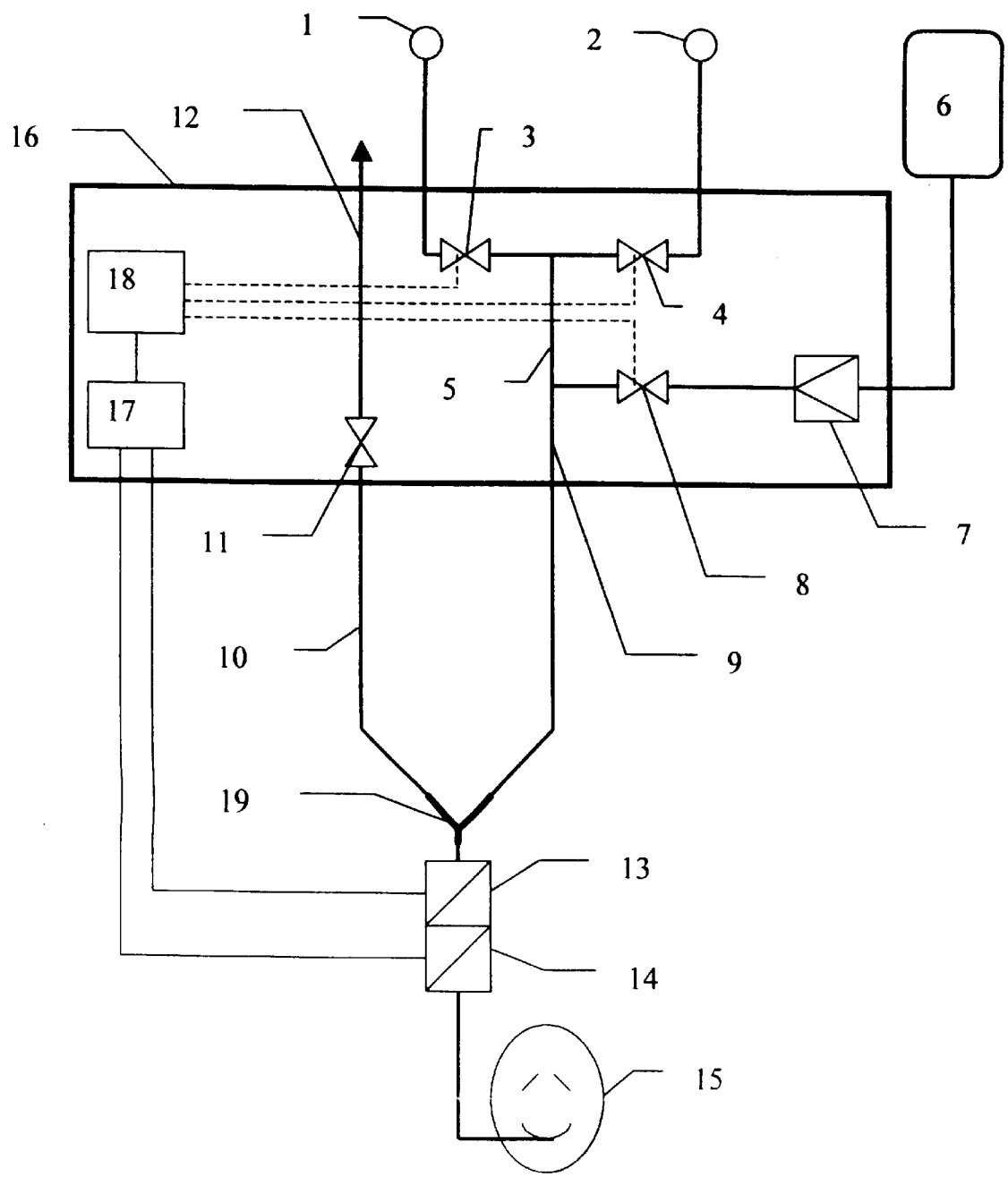
FIG. 1 is a schematic view of a respirator with a patient connected thereto, with which the process according to the present invention can be carried out.

Referring to the drawings in particular, FIG. 1 shows as an example a respirator 16 with a patient 15 connected thereto. The respirator 16 is connected to a compressed air source 1 via a valve 3 and to an oxygen source 2 via a valve 4. The gases are brought together by means of the valves 3 and 4 from the compressed air source 1 and the oxygen source 2 at the desired mixing ratio and with the desired gas volume flow in a line 5. Fluoropropane from a supply cylinder 6 is first adjusted to a constant pressure with a pressure reducer 7 and then fed into the gas volume flow in line 5 via a valve 8. The composition of the gas mixture fed to the patient 15 via the inspiration branch 9, which mixture consists of compressed air, oxygen and fluoropropane, is regulated by means of a computer 18. The valve 3 connected to the compressed air source 1 and the valve 4 connected to the oxygen source 2 are now actuated by the computer 18 such that an oxygen concentration set by the user is obtained. Furthermore, the computer 18 actuates the valve 8, so that the necessary fluoropropane concentration, which is maintained at a constant value during a so-called wash-in phase, becomes established in the inspiration branch 9 of the respiration circuit. This is accomplished by metering the fluoropropane proportionately to the inspiratory volume flow. A gas sensor 14 at the mouthpiece to the patient 15 is used to measure the expiratory fluoropropane concentration K. Whether the expiratory fluoropropane concentration K is measured during the wash-in phase, during the wash-out phase or during both phases depends on the particular method employed to determine the FRC. The inspiratory fluoropropane concentration may optionally also be monitored with the gas sensor 14. The expiratory volume flow i.e., the $$\frac{dV}{dt}$$

volume flow that belongs to the breathing gas volume expired by the patient 15, is measured with a volume flow sensor 13. The values measured by the gas sensor 14 and the volume flow sensor 13 are sent as signals to a measuring unit 17 and are sent to the computer 18 from there. A value for the FRC is calculated in the computer 18 from the measured values for the expiratory fluoropropane concentration K and the expiratory volume flow $$\frac{dV}{dt}.$$

The expired breathing gas is discharged into the environment via the expiration branch 10, the expiration valve 11 and the line 12.

The measurement of the fluoropropane concentration with the gas sensor 14 is performed according to infrared optical measurement methods near the patient at the Y-piece 19 of the respiration circuit 16, and the expiratory volume flow $$\frac{dV}{dt}$$

is determined by the volume flow sensor 13 synchronously. A measuring arrangement is thus available, which is very useful in clinical practice, especially in the treatment of premature and newborn babies, because of its small size and easy handling.

Figure 2:
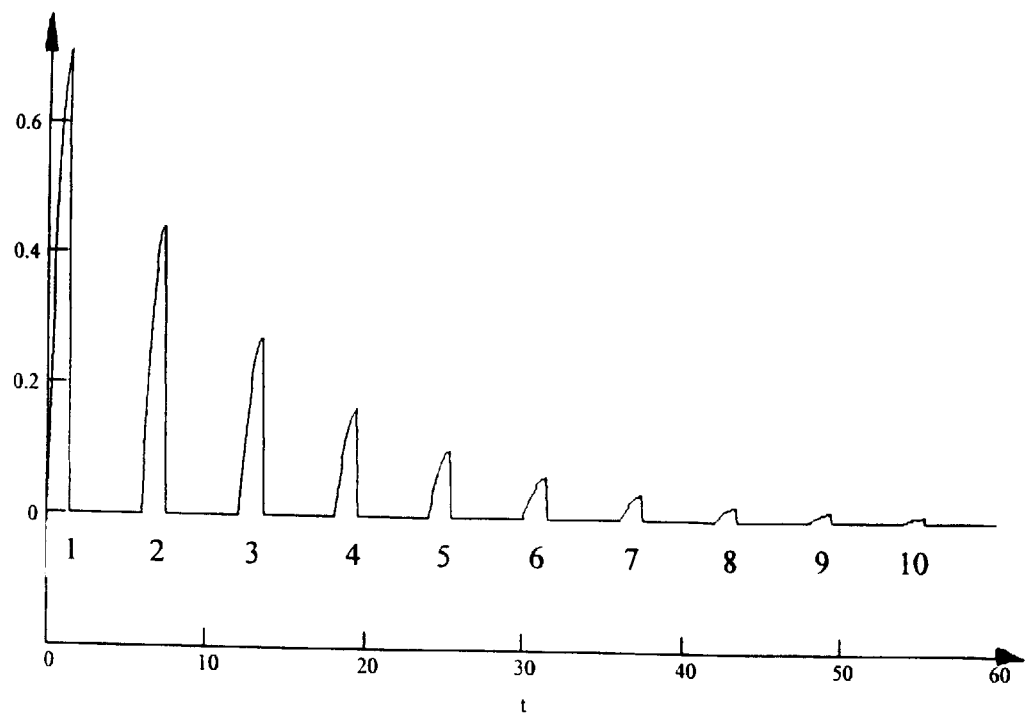
FIG. 2 is the curve showing the fluoropropane concentration over time, which is measured by a gas sensor in the respiration circuit at the mouthpiece to the patient during a wash-out phase.

FIG. 2 shows the curve of the fluoropropane concentration over time, which is measured by the gas sensor 14, in the respiration circuit 16 at the Y-piece 19 to the patient 15 during a wash-out phase. The time t is shown on the abscissa and the fluoropropane concentration in % on the ordinate. The fluoropropane concentration in the patient's lungs is 0.8% at the beginning of the wash-out phase, at time t=0. The lungs were "washed in" before to this value. No more fluoropropane is added to the breathing gas after the end of the wash-in phase and with the beginning of the wash-out phase. Rather, fluoropropane is breathed out during the wash-out phase with each breath A=1, . . . , 10. The maximum expiratory fluoropropane concentration in the expired breathing gas for each breath is indicated in FIG. 2 by the peaks of the curve. The gas sensor 14 at the mouthpiece measures the expiratory fluoropropane concentration in the expired breathing gas, and the computer 18 calculates from this an averaged expiratory fluoropropane concentration $K_1$, . . . , $K_{10}$ for each breath A=1, . . . , 10. The maximum expiratory fluoropropane concentration is already less than 0.8% as a consequence of the wash-out already in the first breath A=1. The fluoropropane concentration drops to zero during the periods between the concentration peaks, when the patient is breathing in via the mouthpiece. The averaged expiratory fluoropropane concentrations $K_1$, . . . , $K_{10}$ in the expired breathing gas decline exponentially during the wash-out phase.

Figure 3:
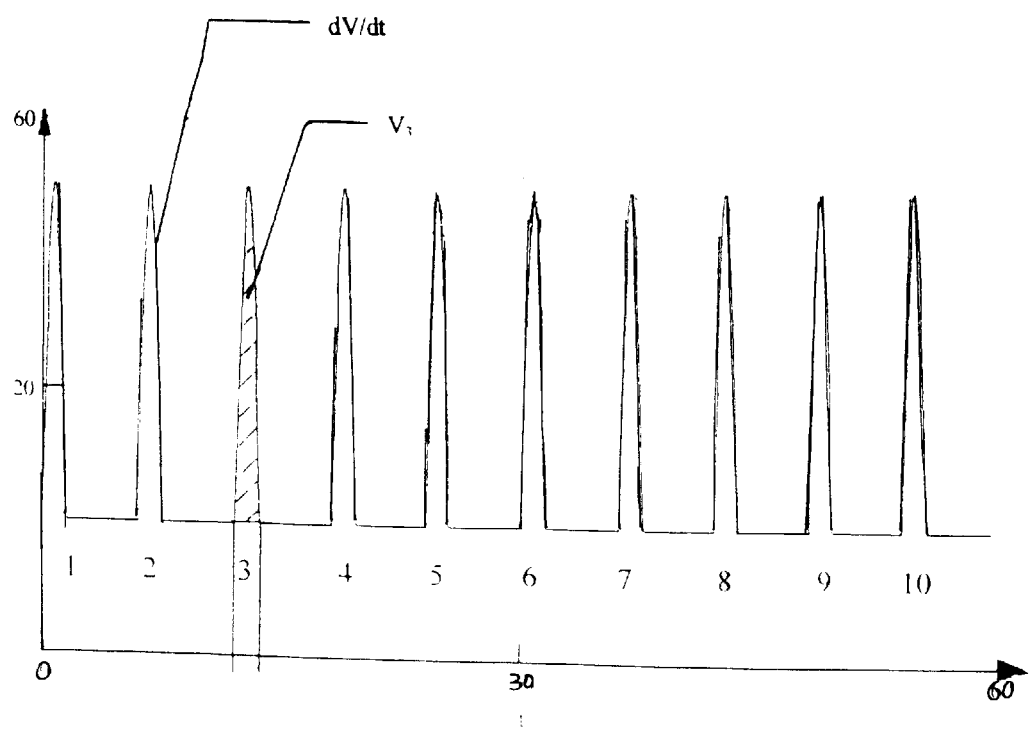
FIG. 3 is the curve of the expiratory volume flow of the expired breathing gas over time, which is measured by a volume flow sensor in the respiration circuit at the mouthpiece to the patient during a wash-out phase.

FIG. 3 shows the curve of the expiratory volume flow over time which is measured by the volume flow sensor 13 in the respiration circuit 16 at the mouthpiece to the patient 15 during the same wash-out phase as in FIG. 2. The time t is shown on the abscissa and the expiratory volume flow $$\frac{dV}{dt}$$

on the ordinate. The volume flow at the times of the inspirations is not taken into account. Instead, the volume flow curve assumes the value zero in FIG. 3 during the inspirations. The expired breathing gas volume can be calculated from this volume flow curve for each breath A=1, . . . , 10 by integrating the volume flow over the time from the beginning of the expiration of the breath A=1, . . . , 10 in question to the end of the expiration. For example, the volume flow $$\frac{dV}{dt}$$

is integrated for breath A=3 from time $t_3$ to time $t_3'$:

$$V_3 = \int_{t_3}^{t_3'} \frac{dV}{dt} dt.$$

A volume $V_1$, . . . , $V_{10}$ of expired breathing gas calculated in this manner for a breath A=1, . . . , 10 during a wash-out phase is multiplied by the corresponding fluoropropane concentration $K_1$, . . . , $K_{10}$ in the expired breathing gas, which is averaged by the computer 18. All the products $V_1 \cdot K_1$, . . . , $V_{10} \cdot K_{10}$ calculated for the respective consecutive breaths A=1, . . . , 10 are subsequently summed up and divided by the difference between the expiratory fluoropropane concentration $K_0$ at the beginning of the wash-out phase and the expiratory fluoropropane concentration $K_{10}$ measured in breath A=10. This calculation leads to an $FRC_{10}$ value for the functional residual capacity:

$$FRC_{10} = \frac{1}{K_0 - K_{10}} \cdot (V_1 \cdot K_1 + \ldots + V_{10} \cdot K_{10})$$

Figure 4:
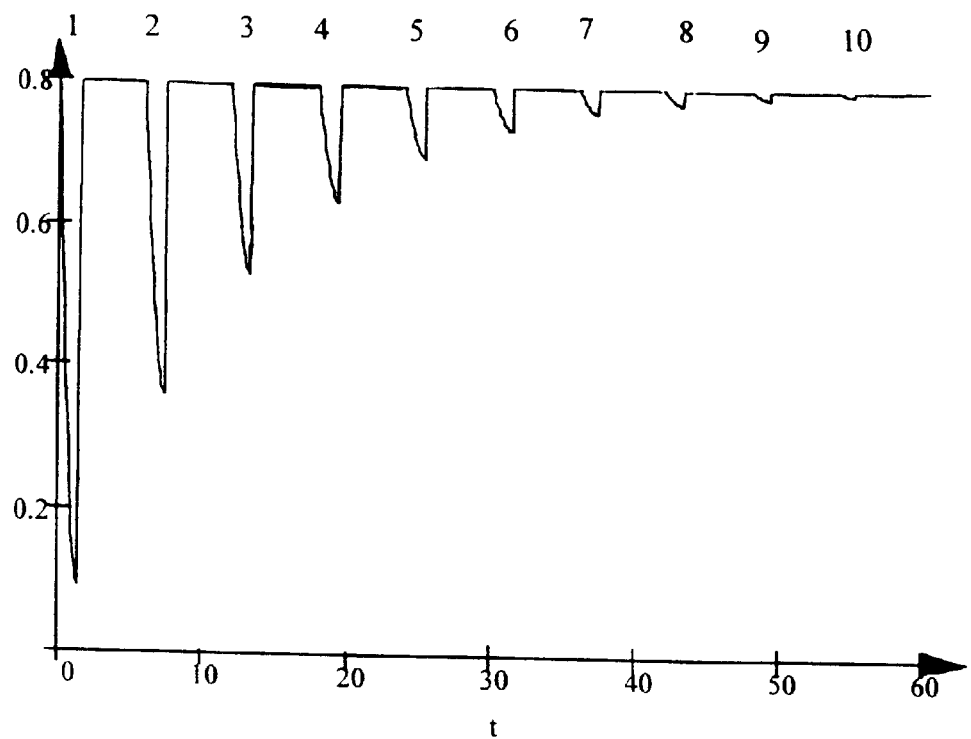
FIG. 4 is the curve of the fluoropropane concentration over time, which is measured by a gas sensor in the respiration circuit at the mouthpiece to the patient during a wash-in phase.

The curve of the fluoropropane concentration over time, which is measured by the gas sensor 14 in the respiration circuit 16 at the Y-piece 19 to the patient 15 during a wash-in period, is shown in FIG. 4. The time t is shown on the abscissa and the fluoropropane concentration in % on the ordinate. The fluoropropane concentration in the lungs of the patient is 0% at the beginning of the wash-in phase, at the time t=0. The lungs are then "washed in" to the concentration value of 0.8%. Fluoropropane is now added with each breath at a constant concentration of 0.8%. The patient expires fluoropropane during this time with each breath A=1, . . . , 10. The minimal expiratory fluoropropane concentrations in the expired breathing gas are represented by the valleys of the curve in FIG. 4. The fluoropropane concentration again rises to 0.8% during the periods between the concentration valleys, when the patient is breathing in via the mouthpiece. The minimal expiratory fluoropropane concentrations in the expired breathing gas increase to the limit value of 0.8% during the wash-in phase in a saturation curve.

The curve showing the expiratory volume flow $$\frac{dV}{dt}$$

of the expired breathing gas over time, which is measured by a volume flow sensor 13 in the respiration circuit at the mouthpiece to the patient during a wash-in phase, corresponds to the curve for a wash-out phase, which is shown in FIG. 3.

While specific embodiments of the invention have been shown and described in detail to illustrate the application of the principles of the invention, it will be understood that the invention may be embodied otherwise without departing from such principles.

What is claimed is:

1. A method of using fluoropropane as a trace gas for determining the functional residual capacity (FRC) of the lungs of a subject during respiration, comprising the steps of:
    washing in fluoropropane to the lungs during a wash-in phase;
    washing out fluoropropane from the lungs during a wash-out phase; and
    monitoring the concentration of fluoropropane in gas exhaled from the lungs during said wash-out phase.

2. A method of using fluoropropane in accordance with claim 1, wherein the fluoropropane is a heptafluoropropane, a hexafluoropropane or a perfluoropropane.

3. A process for determining the functional residual capacity (FRC) of the lungs during respiration of a breathing gas, comprising the steps of:
    introducing via the breathing gas an amount of fluoropropane into the lungs of a patient during a wash-in phase;
    dissipating via the breathing gas said fluoropropane from the lungs of said patient during a wash-out phase; and
    monitoring the concentration of said fluoropropane in the breathing gas at least during said wash-out phase.

4. A process according to claim 3, wherein the fluoropropane is a heptafluoropropane, a hexafluoropropane or a perfluoropropane.

5. A process according to claim 3, further comprising the steps of:
- saturating the lungs with the breathing gas containing a predetermined concentration of fluoropropane as part of said wash-in phase;
- determining corresponding volumes $V_1, \ldots, V_A$ of expired breathing gas for consecutive breaths $A=1, \ldots, n$ during said wash-out phase;
- measuring the fluoropropane concentration in the expired breathing gas using a gas sensor;
- using a computer to determine a mean expiratory fluoropropane concentration $K_1, \ldots, K_A$ for each breath $A=1, \ldots, n$;
- using a computer to calculate a volume of fluoropropane having been expired since a beginning of said wash-out phase for each breath $A=1, \ldots, n$ as a sum of each of the individual said volumes $V_1, \ldots, V_A$ of said expired breathing gas, with said volume $V_1, \ldots,$ multiplied by said corresponding mean fluoropropane concentration $K_1, \ldots, K_A$ of said fluoropropane in these volumes; and
- using said computer to form an $FRC_A$ value for the functional residual capacity (FRC) as a quotient of said expired volume of fluoropropane, and a difference between an end tidal fluoropropane concentration $K_0$ at a beginning of the wash-out phase and a fluoropropane concentration $K_A$ at breath A.

6. A process in accordance with claim 5, further comprising:
- repeating said step of using a computer to calculate a volume of fluoropropane having been expired since a beginning of said wash-out phase and said step of using said computer to form an $FRC_A$ value for the functional residual capacity (FRC) as a quotient of said expired volume of fluoropropane, until a preset number of $FRC_A$ values calculated last are within a preset tolerance range.

7. A process in accordance with claim 6, wherein the preset tolerance range is 5% to 20% of the $FRC_n$ value calculated last.

8. A lung functional residual capacity (FRC) determination system, comprising:
- a respiration arrangement with a patient connection and with an inspiration gas line connected to said patient connection and an expiration gas line connected to said patient connection;
- a breathable gas source connected to said respiration arrangement;
- a fluoropropane gas source connected to said respiration arrangement; and
- a sensor for determining corresponding volumes $V_1, \ldots, V_A$ of expired breathing gas for consecutive breaths $A=1, \ldots, n$ and for measuring a fluoropropane concentration in the expired breathing gas.

9. A system according to claim 8, wherein the fluoropropane is a heptafluoropropane, a hexafluoropropane or a perfluoropropane.

10. A system according to claim 8, further comprising:
- a computer connected to said sensor for determining a mean expiratory fluoropropane concentration $K_1, \ldots, K_A$ for each breath $A=1, \ldots, n$, said computer regulating a flow of the breathable gas into the inspiration gas line and regulating a flow of fluoropropane gas into the inspiration gas line to introduce breathing gas containing a predetermined concentration of fluoropropane into the lungs of the patient during a wash-in phase until the lungs become saturated with the fluoropropane, said computer calculating a volume of fluoropropane having been expired since the beginning of the wash-out phase using, for each breath $A=1, \ldots, n$, a sum of each of the individual volumes $V_1, \ldots, V_A$ of the expired breathing gas, multiplied by the corresponding mean fluoropropane concentration $K_1, \ldots, K_A$ of the fluoropropane in each volumes; and
- said computer forming an $FRC_A$ value for the functional residual capacity (FRC) by the computer as a quotient of the expired volume of fluoropropane, which was calculated and a difference between an end tidal fluoropropane concentration $K_0$ at the beginning of the wash-out phase and the fluoropropane concentration $K_A$ at breath A.

* * * * *